US006747171B2

(12) United States Patent
Rosen

(10) Patent No.: US 6,747,171 B2
(45) Date of Patent: Jun. 8, 2004

(54) LOW TEMPERATURE PURIFICATION OF NAPHTHALENE DICARBOXYLIC ACIDS

(75) Inventor: Bruce I. Rosen, Morton Grove, IL (US)

(73) Assignee: BP Corporation North America Inc., Warrenville, IL (US)

( * ) Notice: Subject to any disclaimer, the term of this patent is extended or adjusted under 35 U.S.C. 154(b) by 0 days.

(21) Appl. No.: 09/775,025

(22) Filed: Feb. 1, 2001

(65) Prior Publication Data

US 2002/0002303 A1 Jan. 3, 2002

Related U.S. Application Data

(60) Provisional application No. 60/179,946, filed on Feb. 3, 2000.

(51) Int. Cl.[7] .......................... C07C 51/42; C07C 51/16
(52) U.S. Cl. ........................ 562/485; 562/416; 562/417; 562/487; 562/485
(58) Field of Search ............................... 562/416, 417, 562/485, 487, 488

(56) References Cited

U.S. PATENT DOCUMENTS

| 3,781,346 | A | * | 12/1973 | Norton ........................ 562/487 |
| 3,888,921 | A | * | 6/1975 | Yamamoto et al. .......... 562/488 |
| 4,794,195 | A | * | 12/1988 | Hayashi et al. .............. 562/414 |
| 4,933,491 | A | * | 6/1990 | Albertins et al. ............ 562/416 |
| 5,081,290 | A | * | 1/1992 | Partenheimer et al. ....... 562/416 |
| 5,256,817 | A | * | 10/1993 | Sikkenga et al. ............ 562/487 |
| 6,160,170 | A | * | 12/2000 | Codignola ................... 562/413 |

* cited by examiner

Primary Examiner—D. Margaret Seaman
Assistant Examiner—Taylor V Oh
(74) Attorney, Agent, or Firm—Nirav Patel

(57) ABSTRACT

A process for purifying a naphthalenic carboxylic acid comprising contacting at a temperature below about 575° F. a mixture comprising an impure naphthalenic carboxylic acid and a solvent in the presence of hydrogen gas with a noble metal on carbon catalyst. The process results in reduced amounts of organic impurities in the purified acid when compared to other purification processes.

19 Claims, 1 Drawing Sheet

US 6,747,171 B2

LOW TEMPERATURE PURIFICATION OF NAPHTHALENE DICARBOXYLIC ACIDS

This application claims the benefit of U.S. provisional patent application Ser. No. 60/179,946, filed Feb. 3, 2000.

BACKGROUND OF THE INVENTION

The invention generally relates to the purification of naphthalenic compounds, and more particularly relates to the purification of naphthalenedicarboxylic acids.

BACKGROUND OF THE INVENTION

Polymers based on dimethyinaphthalenedicarboxylates and their corresponding acids are known to be useful in a wide variety of commercial applications. For example, films made from polymers incorporating dimethyl-2,6-naphthalenedicarboxylate (2,6-NDC) exhibit strength and thermal properties which are superior to films and fibers made from other polymers such as polyethyleneterephthalate (PET). These enhanced properties have led to the use of 2,6-NDC-based polymers in camera films and magnetic recording tapes as well as electrical and electronic components.

2,6-NDC-based polymers also exhibit high resistance to the diffusion of gases such as carbon dioxide, water vapor and oxygen. This resistance to gas diffusion makes these polymers useful in films and containers for a wide variety of food and beverage packaging applications.

The superior physical strength of 2,6-NDC-based polymers also renders these polymers useful in physically demanding applications such as cords for automobile and motorcycle tires.

The use of 2,6-naphthalenedicarboxylic acid in such applications provides several advantages over 2,6-NDC. First, the weight differences between the acid and the ester typically results in higher yields of polymer per pound of feedstock. Additionally, polymerization of the acid with ethylene glycol produces water, rather than the more difficult to handle methanol produced when the ester is polymerized with ethylene glycol. Furthermore, in polymer plants already designed to handle only acid-type monomers, use of the acid permits the addition of naphthalenedicarboxyl moieties to polymers which could not be accomplished if only the ester form was available.

The production and direct purification of an acid monomer also greatly simplifies monomer production. Specifically, in the synthesis of 2,6-NDC, 2,6-dimethylnaphthalene (2,6-DMN) is oxidized to produce 2,6-naphthalenedicarboxylic acid (2,6-NDA), which must subsequently be esterified to produce 2,6-NDC, with one or more purification steps such as distillation or recrystallization being performed in one or both of those steps as necessary to produce a product having a high yield and purity. In contrast, direct purification of the oxidation product of 2,6-DMN is relatively simple, and can therefore result in a lower cost monomer.

Unfortunately, the purification of 2,6-NDA typically has been conducted at temperatures at or in excess of 600 degrees Fahrenheit to permit the processing of a relatively high percent of total dissolved solids. Operating at these temperatures requires substantial capital investment in plants capable of withstanding the pressure resulting from operating at these temperatures. Furthermore, operating at these temperatures requires a large investment in energy to heat the reaction mixtures to the required 600+ degree Fahrenheit temperature. Finally, even when operating at these preferred conditions, impurities present in the purified monomer may require additional purification before they are useful in polymer applications.

What is needed is a relatively inexpensive way to purify naphthalenic diacid monomer more efficiently and at low cost, and which results in a lower level of impurities than is presently produced in the typical high temperature purification processes presently used.

SUMMARY OF THE INVENTION

We have found that naphthalenic diacid monomers can be efficiently produced by operating at lower temperatures and solids loadings levels than have been typically used in commercial practice. Surprisingly, when the proper catalyst and operating conditions are selected, monomer having lower levels of undesired impurities is obtained, thereby decreasing the need for further purification of the acid monomer.

Additionally, because these reactions are performed at lower temperatures, we have found that underutilized chemical plant assets designed for less strenuous operating conditions, such as those used to purify terephthalic acid, may be employed to purify diacid monomers such as 2,6-NDA. Utilizing such existing assets can eliminate capital costs associated with building a plant capable of operating at the 600+ degree Fahrenheit temperature typically used commercially for NDA purification, thereby further enabling relatively inexpensive production of the monomer.

DETAILED DESCRIPTION OF THE PREFERRED EMBODIMENTS

Figure 1:
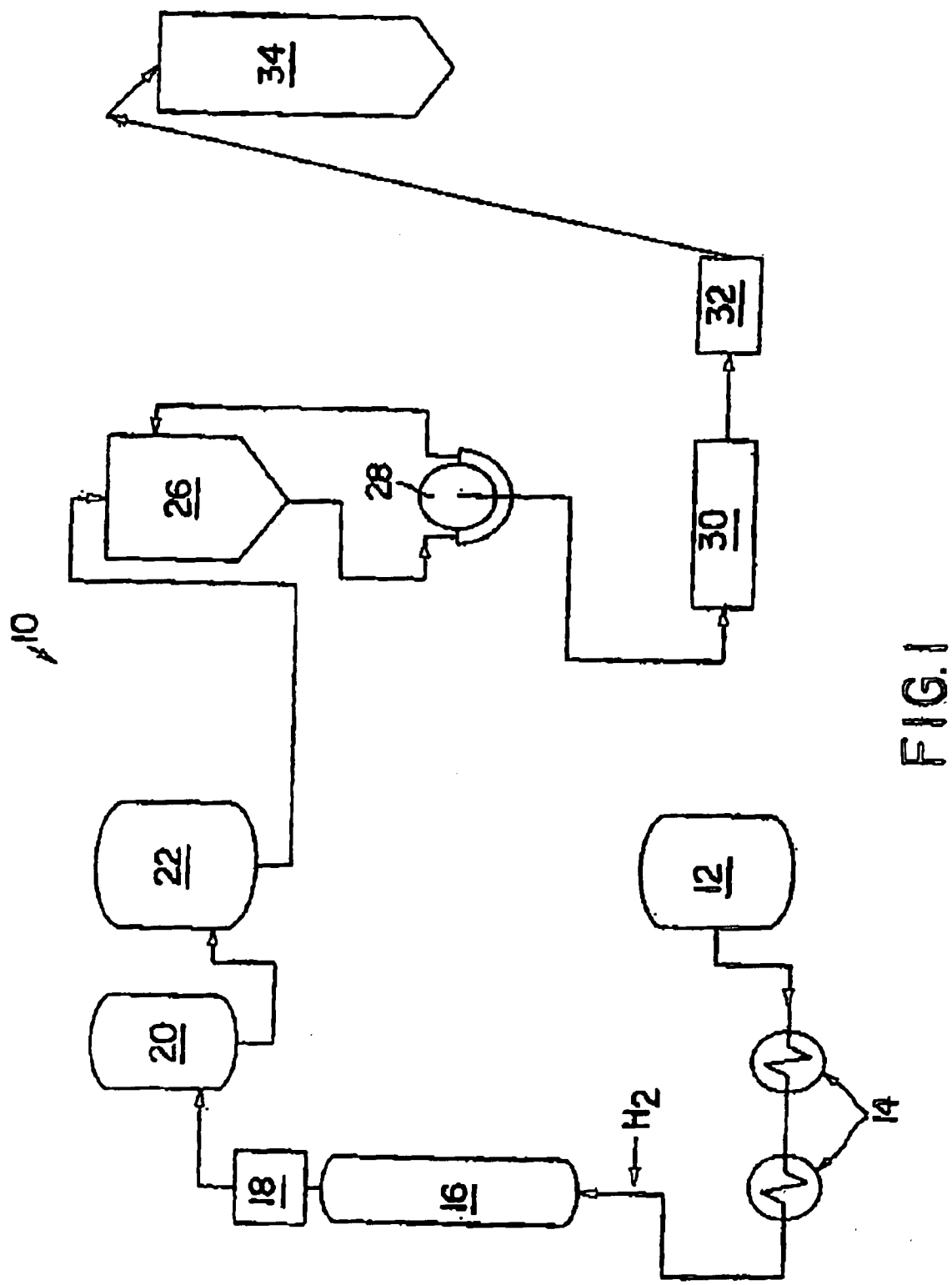
FIG. 1 is a flow diagram of a process for purifying 2,6-naphthalenedicarboxylic acid.

The following detailed description compares purification of 2,6-naphthalenedicarboxylic acid prepared under typical high temperature conditions to low temperature purification of the same acid under conditions which can be accomplished in other chemical processing plants, such as those used for the purification of terephthalic acid. The discussion is illustrative only. Other embodiments of the invention will be apparent to those skilled in the art after reviewing the following descriptions. For example, I believe my invention is well-suited to the purification of other similar diacids such as 1,5-naphthalenedicarboxylic acid, as well as other naphthalenic acids having acid functionalities of one or more. The description, therefore, is not intended in any way to limit the scope of our invention.

Generally, I have found that my process yields naphthalenic acid monomers containing lower residual amounts of undesired naphthalenic compounds that can react under polymerization conditions to branch or terminate polymer chains. This advantage can be obtained by operating at lower temperatures and solids concentrations than have been used commercially to purify such acids. Additionally, the proper selection of noble metal catalyst can substantially enhance the quality of the purified acid produced by the process.

Specifically, the purification process should be carried out at temperatures between about 520 and 575° F., preferably 525 and 560° F., and most preferably at 550° F. Total dissolved solids should be the maximum weight percent of 2,6-NDA soluble at the reaction temperature, which will range from 3.9% at 520° F. to 12% at 575° F., 4.4% at 525° F. and 10% at 560° F., and which is about 7% at 550° F.

It should be noted that in the temperature and solids loading ranges of the invention, it is expected that at higher separation temperatures, 2,6-NDA yield will be less but the relative amount of organic impurities will decrease, while at lower temperatures, yield and relative amounts of organic impurities may increase.

Furthermore, I have found that use of this process enables the use of other purification facilities such as terephthalic acid purification facilities. This is unexpected, as it is generally believed that naphthalenic acids are preferably purified at 600° F.+ to increase the amount of dissolved solids present in the purification reactor feedstock.

The combination of these discoveries means that naphthalenic acids can be purified to a greater degree in facilities previously thought to be unsuitable or undesirable for such work. Use of the process can therefore result in lower capital and energy costs for new plants, or the use of existing facilities such as PTA purification reactors for the production of high quality naphthalenic acid monomers.

The term "low temperature reactor vessel" will be used herein to refer to a vessel designed for a nominal operating temperature of less than 600° F. and its corresponding pressure when purifying an acid monomer in a substantially aqueous solvent. "Nominal operating temperature" means the temperature at which the vessel is designed to operate on a continuous basis, rather than a number such as the maximum operating temperature, which typically may be required by the relevant engineering standard to be 1.5 to 2 times the nominal operating temperature.

FIG. 1 is a flow diagram of a semi-works scale naphthalenic acid purification plant 10 used in Comparative Example 1 and Example 1 to produce large quantities of 2,6-naphthalenedicarboxylic acid.

Plant 10 purifies a crude 2,6-NDA feedstock produced by the liquid phase oxidation of 2,6-DMN in the presence of a source of molecular oxygen, a solvent comprising a monocarboxylic acid and water. The reaction used to produce the acid feedstock typically is conducted in the presence a catalyst comprising cobalt, manganese and bromine components, at reaction temperatures of from about 100 to 260° C. The reaction preferably is performed in a monocarboxylic acid solvent such as acetic acid, or a mixture of acetic acid and water, with a ratio of solvent to DMN of about 2:1 to 12:1, a manganese to cobalt ratio of about 5:1 to 0.3:1, a bromine to manganese plus cobalt ratio of about 0.3:1 to 0.8:1, and a total amount of cobalt plus manganese of up to one weight percent of the selected solvent. Additional information concerning the oxidation of DMN's to NDA's can be found in our U.S. Pat. No. 5,292,934 to Sikkenga et al. and U.S. Pat. No. 5,254,719 to Holzhauer, et al., the disclosures of which are incorporated by reference.

Plant 10 purifies the crude 2,6-NDA feedstock in the following manner. Slurried feedstock from vessel 12 is heated to the desired operating temperature through a series of steam and hot oil preheaters 14 as it passes into a fixed bed hydrogenation reactor 16. In reactor 16, the crude feedstock is treated in the presence of hydrogen and a hydrogenation catalyst. Hydrogenated effluent from reactor 16 passes through a wound carbon filter 18 to remove catalyst fines and other small particulate matter. Next, the filtered effluent is crystallized in crystallizers 20 and 22.

Overheads from crystallizers 20 and 22 are collected and routed to waste treatment facilities, while the solution in crystallizers 20 and 22 is transferred to rotary drum filter feed tank 26 and filtered in rotary drum filter 28. Filter cake from rotary drum filter 28 constituting the purified 2,-NDA is dried in rotary drier 30, cooled in cooler 32 and transferred to storage silo 34 for packaging and shipment.

COMPARATIVE EXAMPLE 1

Hydrogenation reactor 16 was charged with 1,408 pounds of peat carbon available from Norit Americas, Inc. as Norit ROX 0.8, an extruded 0.8 mm diameter activated carbon that has been acid washed and which has an apparent bulk density of 25.5 pounds per cubic foot.

A slurry of crude 2,6-NDA feedstock having the specifications set forth in Table 1A, below, was prepared in feed vessel 12 at a temperature of approximately 120° F.

TABLE 1A

| Crude 2,6-NDA Feedstock Specifications | |
|---|---|
| Purification Solvent | water |
| Average Weight Percent Total Dissolved Solids | 12% |
| Weight percent 2,6-NDA as percent of Total Dissolved Solids | 96% |
| 6-formyl-2-napthoic acid ("FNA") (as ppmw total solids) | 1,120 |
| 1-bromo-2,6-naphthalenedicarboxylic acid ("BrNDA") (as ppmw total solids) | 1,477 |

The feedstock was heated in preheaters 14 to a temperature of 600° F. and reacted in hydrogenation reactor 16. Feed rates were approximately 14–15 gallons per minute, with a total solids concentration in the feed averaging about 12 weight percent.

Filtered reactor effluent was crystallized in crystallizers 20 and 22 by evaporative cooling of the effluent. The crystallizer effluent was washed twice with water, filtered at a temperature between about 300 and 400° F., the crystallized acid slurried in water and filtered on a rotary vacuum filter 28 at ambient pressure, and dried at a temperature of about 250° F. for 60 minutes in rotary drier 30. The dried, purified NDA had the specifications, when averaged over 7 approximately 20,000 pound batches, as set forth in Table 1B, below.

TABLE 1B

| Specifications of Purified 2,6-NDA | |
|---|---|
| Weight percent 2,6-NDA (as weight percent of total solids) | 99.8 |
| 6-formyl-2-napthoic acid ("FNA") (as ppmw total solids) | 23 |
| 1-bromo-2,6-naphthalenedicarboxylic acid ("BrNDA") (as ppmw total solids) | not detected (<20 ppmw) |
| 2-napthoic acid ("2-NA") (as ppmw total solids) | 106 |
| 6-methyl-2-napthoic acid ("6-Me-2-NA") (as ppmw total solids) | 130 |
| 2,6-dicarboxytetralin ("2,6-DCT") (as ppmw total solids) | 488 |
| Trimellitic acid ("TMLA") (as ppmw total solids) | not detected (<10 ppmw) |

As can be seen from the data in Table 1B, several naphthalenic impurities were detected in the purified acid.

Example 1, below, demonstrates the advantage of operating at lower temperatures using a noble metal catalyst.

EXAMPLE 1

Hydrogenation reactor 16 was charged with 1,369 pounds of a catalyst having 0.5 weight percent palladium (as total catalyst weight) on a 4×8 mesh granular carbon support available from Engelhard Corporation. As in Comparative Example 1, a slurry of crude 2,6-NDA feedstock having the specifications set forth in Table 1A, below, was prepared in feed vessel 12 at a temperature of approximately 120° F.

The feedstock was heated in preheater 14 to a temperature of between 525 and 565° F. and reacted in hydrogenation reactor 16. Feed rates were approximately 13 to 16 gallons per minute, with a total solids concentration in the feed of from 4 to 6.5 weight percent.

Filtered reactor effluent was crystallized in crystallizers 20 and 22 by evaporative cooling of the effluent. The crystallizer effluent was washed twice with a water filter at a temperature between about 310 and 345° F., and the crystallized acid slurried in water and filtered on a rotary vacuum filter 28 at ambient pressure, and dried at a temperature of about 250° F. for 60 minutes in rotary drier 30. The dried, purified NDA had the specifications, when averaged over 4 approximately 20,000 pound batches, as set forth in Table 2, below.

TABLE 2

Specifications of Purified 2,6-NDA

| | |
|---|---|
| Weight percent 2,6-NDA (as weight percent of total solids) | 99.9 |
| 6-formyl-2-napthoic acid ("FNA") (as ppmw total solids) | not detected (<8 ppmw) |
| 1-bromo-2,6-naphthalenedicarboxylic acid ("BrNDA") (as ppmw total solids) | not detected (<20 ppmw) |
| 2-napthoic acid ("2-NA") (as ppmw total solids) | 124 |
| 6-methyl-2-napthoic acid ("6-Me-2-NA") (as ppmw total solids) | 10 |
| 2,6-dicarboxytetralin ("2,6-DCT") (as ppmw total solids) | not detected (<10 ppmw) |
| Trimellitic acid ("TMLA") (as ppmw total solids) | not detected (<10 ppmw) |

As can be seen by comparing the data from Table 1B to the data in Table 2, no FNA, BrNDA, TMLA or 2,6-DCT were detected in the purified acid. All of these impurities are considered to be harmful in the polymerization of 2,6-NDA monomer when present in sufficient amounts, and the absence of these impurities in the low temperature, Pd/C catalyzed purification process of the present invention results in a commercially preferred process for this reason.

Catalytic metals useful in the inventive process include Group VIII noble metals, preferably palladium, platinum and ruthenium. As will be demonstrated in Example 2, below, the purification process provided surprisingly better results when the selected metal was palladium.

The noble metal may be supported on any inert support which remains stable under the stated process conditions, such as carbon or the rutile phase of titanium dioxide. The preferred supports are activated carbons such as nutshell carbons, although granular carbons will work. The noble metal should be present in an amount of from about 0.1 to 3.0 percent of total catalyst weight, more preferably 0.35 to 0.8 percent of total catalyst weight, and most preferably about 0.5 percent of total catalyst weight. The preferred catalyst is about 0.5 weight percent palladium on a nutshell carbon support.

The surprising superiority of a palladium catalyst on a carbon support in my process is demonstrated by Example 2, below.

EXAMPLE 2

Bench scale comparisons of 2,6-NDA purification using palladium on carbon, ruthenium on carbon, and platinum on carbon catalysts were performed under conditions simulating purification of 2,6-NDA in a terephthalic acid purification process plant where the purification reactor was designed for operation at a nominal operating temperature of no greater than about 550° F. The comparison was designed to screen various noble metals for their relative efficiency in reducing the amount of color, and the amount of DCT and 2-NA produced using the purification process of my invention.

Continuous hydrogenations were performed in a fixed bed reactor. Typical reaction conditions were 550° F. and 6.25 weight percent total solids. The reactor size was 75 cubic centimeters and the feed rate was between 7 and 12 grams per minute, with a hydrogen flow rate of 3 to 10 milliliters per minute.

Total reactor solid effluent was recovered and analyzed for organics by liquid chromatography, and the total reactor effluent was filtered at 140° F. and dried and the filter cake was analyzed for color.

The results of these comparisons are summarized in Table 3, below.

TABLE 3

| Catalyst | L* | b* | 2-NA (wt. % of total reactor effluent) | DCT (wt. % of total reactor effluent) |
|---|---|---|---|---|
| 0.5 wt. o/o Pd/C | 96.4 | 8.16 | 0.23 | 4.9 |
| 1.0 wt. % Ru/C | 94.5 | 6.06 | 6.2 | 3.5 |
| 0.5 wt. % Pt/C | 94.4 | 7.83 | 5.8 | 7.2 |

As can be seen from the data in Table 3, the palladium on carbon catalyst yielded a purified acid product containing about one half the total impurities resulting from the use of the ruthenium catalyst and one-third of the total impurities produced resulting from the use of the platinum catalyst. Furthermore, while both palladium and ruthenium were approximately twice as effective as platinum in reducing the amount of DCT present in the reactor effluent, palladium was the only noble metal to provide substantial reductions in both 2-NA and DCT. No substantial color effects were observed.

Additional benefits may be obtained by modifying the Group VIII metal catalyst of my invention by adding about 0.1 to 2.5 weight percent, and preferably about 0.2 to 0.6 weight percent, of a Group IVB metal selected from the group consisting from silicon, germanium, tin or lead as illustrated in Example 4, below.

EXAMPLE 4

The ruthenium on carbon catalyst of Example 3 was modified by adding 0.4 weight percent of tin measured as weight percent of the total catalyst. The experiment of Example 3 was repeated under the same conditions. As can be seen from Table 4, below, incorporating tin reduced the amount of DCT present in the total reactor effluent by a factor of 5, and the amount of 2-NA present in the total reactor effluent by about 25%.

TABLE 4

| Catalyst | 2-NA (wt. % of total reactor effluent) | DCT (wt. % of total reactor effluent) |
|---|---|---|
| 1.0 wt. % Ru/C | 6.2 | 3.5 |
| 1.0 wt. % Ru/C + 0.4 wt. % Sn | 4.7 | 0.71 |

The surprising reduction in DCT accomplished by modifying the ruthenium on carbon catalyst in a low temperature reactor in accordance with the present invention shows that Group IVB modified noble metal catalysts can provide purified acid monomers having substantially reduced amounts of DCT.

I claim:

1. A process for purifying a naphthalenic carboxylic acid selected from the group consisting of 2,6-naphthalenedicarboxylic acid and 1.5-naphthalenedicarboxylic acid comprising contacting an impure naphthalenic acid and a purification solvent selected from the group consisting of water or mixtures of acetic acid and water in the presence of hydrogen with a catalyst comprising, in combination, a Group VIII noble metal selected from the group consisting of palladium, platinum, and ruthenium, with a Group IVB metal selected from the group consisting of silicon, germanium, tin, or lead, at a purification temperature of from about 520 to 575° F.

2. The process of claim 1 wherein the naphthalenic carboxylic acid is 2,6-naphthalenedicarboxylic acid.

3. The process of claim 1 wherein the noble metal is palladium.

4. The process of claim 1 wherein the noble metal is deposited on a carbon support.

5. The process of claim 1 wherein the acid is 2,6naphthalenedicarboxylic acid prepared by the liquid phase, heavy metal catalyzed oxidation of 2,6-dimethylnaphthalene.

6. The process of claim 1 wherein the noble metal is palladium on a carbon support, and wherein the naphthalenic carboxylic acid is 2,6-naphthalenedicarboxylic acid.

7. The process of claim 6 wherein the 2,6-naphthalenedicarboxylic acid for purification is prepared by the liquid phase, heavy metal catalyzed oxidation of 2,6-dimethylnaphthalene.

8. The process of claim 1 wherein the purification temperature is about 525° F.

9. The process of claim 1 wherein the total percent dissolved solids in the purification solvent is less than twelve weight percent, based on the total weight of solids plus solvent.

10. The process of claim 7 wherein the total percent dissolved solids in the purification solvent is less than ten weight percent, based on the total weight of solids plus solvent, and wherein the purification temperature is about 525° F. to about 560° F.

11. The process of claim 1 which is performed in a purification reactor designed to operate at a normal temperature no greater than about 550° F.

12. The process of claim 6 which is performed in a purification reactor designed to operate at a nominal operating temperature no greater than about 550° F.

13. The process of claim 10 which is performed in a purification reactor designed to operate at a nominal operating temperature no greater than about 550° F.

14. The process of claim 1 wherein the purified acid is recovered by solid liquid separation at a temperature of between about 300 and 340° F.

15. The process of claim 6 wherein the purified acid is recovered by solid liquid separation at a temperature of between about 300 and 340° F.

16. The process of claim 10 wherein the purified acid is recovered by solid liquid separation at a temperature of between about 300 and 340° F.

17. The process of claim 1 wherein the Group IVB metal is tin.

18. The process of claim 1 wherein the Group IVB metal is present at between 0.2 and 0.6 weight percent of the total catalyst weight.

19. The process of claim 17 wherein the tin is present at between 0.2 to 0.6 weight percent of the total catalyst weight and the noble weight is ruthenium, which is present at between 0.1 to 3.0 weight percent total catalyst weight.

* * * * *